(12) United States Patent
Cruz et al.

(10) Patent No.: US 6,245,785 B1
(45) Date of Patent: Jun. 12, 2001

(54) DISSOLUTION OF TRIPROLIDINE HYDROCHLORIDE

(75) Inventors: Victor A. Cruz, Newark; W. Michael Nichols, Fanwood; Albert F. Sorg, Columbia; George E. Tortarolo, Bridgewater; William Bess, Edison; Neema Kulkarni, Randolph, all of NJ (US)

(73) Assignee: Warner Lambert Company, Morris Plains, NJ (US)

( * ) Notice: Subject to any disclaimer, the term of this patent is extended or adjusted under 35 U.S.C. 154(b) by 0 days.

(21) Appl. No.: 09/201,250

(22) Filed: Nov. 30, 1998

(51) Int. Cl.$^7$ .................................................. A61K 31/44
(52) U.S. Cl. ........................................................ 514/343
(58) Field of Search ............................................. 514/343

(56) References Cited

U.S. PATENT DOCUMENTS

| 2,712,020 | 6/1955 | Adamson | 260/294.8 |
| 2,712,023 | 6/1955 | Adamson | 260/296 |

FOREIGN PATENT DOCUMENTS

| WO9207559 | 5/1992 | (WO) . |
| WO9621431 | 7/1996 | (WO) . |
| WO9746243 | 12/1997 | (WO) . |

OTHER PUBLICATIONS

Chemical Abstracts 121:148233, Jung, 1992.*
Chemical Abstracts 89:204231, Augstein, 1978.*
Chemical Abstracts 129:8597, abstract of VanLengerich, WO 9818610, May 1998.*
Chemical Abstracts 120:315629, Gibson, abstract of Br. J. Pharmacol., vol. 111(4), pp1262–1268, 1994.*
Chemical Abstracts 116:147517, abstract of EP 459387, 1991, Dubler.*
"Rote Liste 1996"; 1996; Edition Cantor; Aulendorf, Germany.

* cited by examiner

*Primary Examiner*—D. Margaret Seaman
(74) *Attorney, Agent, or Firm*—Evan J. Federman

(57) ABSTRACT

The present invention is directed to pharmaceutical compositions containing triprolidine and an ionic additive that improves the measured availability of the triprolidine in the tablet, as indicated by standard USP assay for triprolidine in pharmaceutical compositions. The invention also provides a process for producing compositions having improved triprolidine availability and a process for improving the performance of a pharmaceutical composition in a dissolution assay measuring triprolidine availability. The ionic additive can be, for example, an alkali metal salt, such as sodium chloride or potassium chloride.

18 Claims, No Drawings

DISSOLUTION OF TRIPROLIDINE HYDROCHLORIDE

BACKGROUND OF INVENTION

1. Field of the Invention

The present invention relates to pharmaceutical compositions comprising triprolidine, and more particularly to tablets containing triprolidine hydrochloride and processes for producing and assaying such tablets.

2. Background of the Invention

Triprolidine hydrochloride monohydrate is a monograph/compendial antihistamine contained in a variety of pharmaceutical products. The compound and methods for producing it are disclosed by Adamson in U.S. Pat. Nos. 2,712,020 and 2,712,023 and by Adamson et al., *J. Chem. Soc.* 312 (1958). A more recent publication describing triprolidine and methods for producing it is *Analytical Profiles of Drug Substances*, Vol. 8, pp. 509–528 (Florey, Ed., Academic Press, N.Y., 1979).

Triprolidine demonstrates unusual behavior when used in certain pharmaceutical preparations. Due to its low dose and to insure content uniformity, triprolidine is normally wet processed with standard pharmaceutical excipients, then dried and tableted. The commonly used excipients are starches, sugars and celluloses. The formulations prior to tableting contain the expected level of triprolidine with good content uniformity.

However, when the tablets are evaluated using the required United States Pharmacopeia dissolution assays (*United States Pharmacopeia 23/The National Formulary 18*, pp. 1606–1608 (1994)), only 85% to 90% of the triprolidine appears to dissolve. This behavior is noted even though all of the individual components of the tablet are extremely water soluble. This type of dissolution has even been observed with simple triprolidine granulations prior to compressing them into a tablet. In the past, this 85%–90% release level was largely acceptable because the USP dissolution S-1 acceptance criterion (i.e., tolerance) was 80%. However, as USP is raising the minimum tolerance level to 85%, batches formally considered acceptable will now be borderline at best.

Thus, a need exists to improve the performance of triprolidine compositions in USP testing. A need also exists to improve the availability of triprolidine hydrochloride in tablets prepared by, e.g., wet granulation or direct compression, and tested according to USP standards.

All references cited herein are incorporated by reference herein in their entireties.

SUMMARY OF THE INVENTION

The present invention addresses at least the foregoing problems in the art by providing a pharmaceutical composition comprising triprolidine and an ionic additive effective to increase triprolidine availability indicated by a dissolution assay.

Also provided are a process for preparing the composition of the invention and a process for improving a performance of a pharmaceutical composition in a dissolution assay measuring triprolidine availability, said process comprising incorporating into said composition an ionic additive in an amount effective to increase said triprolidine availability measured by said dissolution assay.

DEFINITIONS

The term "ionic additive" denotes a highly ionic, water soluble material added to triprolidine compositions to improve the triprolidine availability in standard assays.

The term "highly ionic" denotes a compound that is substantially completely ionized in aqueous solution.

The term "water soluble" is defined in accordance with the USP definition for solubility at page 2071 of USP23/NF18. That is, a solute is water soluble for purposes of this disclosure if not more than about 30 parts of solvent are required to dissolve 1 part of solute.

The term "triprolidine" as used herein encompasses the compound itself and salts thereof, including, e.g., triprolidine hydrochloride, triprolidine sulfate and triprolidine citrate. This disclosure largely focuses on triprolidine hydrochloride, as the form of triprolidine presently approved by USP for pharmaceutical use.

DETAILED DESCRIPTION OF THE INVENTION

The invention enables improving the performance of triprolidine compositions in standard assays for triprolidine. In standard USP tests for triprolidine, compositions according to the invention tend to show a higher percentage of triprolidine available than prior art compositions. Thus, the invention helps to insure that the dissolution of triprolidine exceeds the requirements of both current and proposed monographs.

The inventors have surprisingly discovered that adjusting the formula of the composition to include an ionic additive can increase the availability of triprolidine from compositions. The ionic additive is preferably an alkali metal salt, more preferably an alkali metal salt of a halogen, even more preferably a chloride salt of an alkali metal, and most preferably sodium chloride. Non-limiting examples of suitable ionic additives include sodium chloride, potassium chloride, sodium bromide, potassium bromide, sodium iodide, potassium iodide and the like.

The ionic additive (or mixture of ionic additives) is preferably incorporated into a tablet formulation in an amount effective to increase the availability of triprolidine in tablets produced from the formulation without unduly compromising the safety of the tablets (as at least some of the ionic additives are toxic at high enough levels, as known in the art). Preferably, the amount of ionic additive(s) added should be effective to raise the percentage of triprolidine available from tablets above 90% and more preferably above 94%. In embodiments, the ionic additive(s) can preferably be added in an amount ranging from about 10 to about 50 wt. %, more preferably about 20 to about 40 wt. %, even more preferably about 26 to about 30 wt. %, based on the total weight of the formulation other than coatings. The ionic additive can be substituted for sugar excipients, such as lactose, in conventional wet granulation formulations (or direct compression formulations) to provide formulations according to this invention.

The availability of triprolidine (hereinafter sometimes referred to as "triprolidine availability") is defined by performing the USP triprolidine assay on tablets dissolved in water. Triprolidine availability is expressed in terms of a percentage of triprolidine detected in solution relative to an amount of triprolidine theoretically present in each tablet. Thus, if 2 mg of triprolidine is theoretically present in a tablet, but only 1.9 mg is detected in solution, then the triprolidine availability for the tablet is 1.9/2.0 or 95%.

Without wishing to be bound by any theory, the inventors believe that the improved availability of triprolidine can be explained as follows. Triprolidine hydrochloride's preferred or most stable form is the monohydrate. In the drying step of the wet granulation process, it is postulated that hydrogen bonds are formed with the hydroxyl groups present in the various excipients, e.g., lactose and starch, to form association complexes. During the vigorous extraction conditions used in the product assay, these hydrogen bonds with the excipients are disrupted, the association complexes destroyed, and the unassociated drug released. The detection system used in the assay method has been tuned to measure the level of free or unassociated drug in solution. Since only free drug is present in the system, the analytical test results agree very well with the theoretical values. The method does not detect/accurately measure the associated drug.

Under the milder conditions of the dissolution test, the hydrogen bonds are not cleaved. The association complexes remain intact so the triprolidine hydrochloride is not released. Since only free drug is measured, the analytical test results, when compared with the theoretical concentration, are low. Addition of the ionic material to the product causes a highly ionic solution in the micro-environment of the area of tablet dissolution. This environment causes the breakdown of the association complexes and the release of the free drug so that it is readily detected and measured.

In order to prepare a solid dosage form containing one or more active ingredients (such as triprolidine), it is necessary that the material to be compressed into the dosage form possess certain physical characteristics that lend themselves to processing in such a manner. Excipients can assist in this regard.

Preferably, tablets of the invention include excipients such as, e.g., lubricants, diluents, binders (e.g., starch and sugars such as sucrose, glucose, dextrose, and lactose) and/or disintegrants (e.g., starch derivatives and salts of carboxymethylcellulose, processed forms of cellulose, sugars, and dicalcium phosphate dihydrate).

Pharmaceutically active agents in addition to triprolidine can be incorporated into the product of the invention. Such agents are not particularly limited, except that they are preferably compatible with triprolidine. Non-limiting examples of suitable agents include decongestants (e.g., pseudoephedrine), cough suppressants (e.g., dextromethorphan), and pain relievers (e.g., NSAIDs, such as acetaminophen and the like). Such agents are preferably included in the final tableted product in pharmaceutically effective amounts.

The tablets can be coated or uncoated. Non-limiting examples of suitable coatings include candelilla wax, hydroxypropyl-based cellulosic-based or sugar-based coatings. Such coatings are preferably coated on the final tableted product in amounts of about 1–3 wt. % in the case of a film coating or at least about 50 wt. % in the case of a sugar-based coating.

The invention will be illustrated in more detail with reference to the following Examples, but it should be understood that the present invention is not deemed to be limited thereto.

EXAMPLES

Example 1

A granulation batch was prepared with the following ingredients:

| Ingredient | Quantity (grams) | Percent of Total |
| --- | --- | --- |
| Triprolidine HCl | 137.50 | 2.01 |
| Pseudoephedrine HCl | 3300.00 | 48.21 |
| Sodium Chloride | 3272.50 | 47.81 |
| Povidone (K29–32) | 135.00 | 1.97 |

All dry ingredients were delumped prior to use. All the ingredients except the povidone were dry blended. The povidone was added as a 30% aqueous solution and the batch was mixed to uniformity. The wet granulation was wet sized and then dried. The dried granulation was dry sized to match the particle size of the remaining dry tablet ingredients. A portion of the resulting granulation batch was assayed for triprolidine content and pseudoephedrine content by standard USP assays. The results are shown in Table A.

Example 2

Tablets having the following core ingredients were prepared:

| Ingredient | Quantity (grams) | Percent of Total |
| --- | --- | --- |
| Granulation Batch of Example 1 | 2488.80 | 59.2571 |
| Poloxamer 407 | 100.00 | 2.381 |
| Polyethylene Oxide (N-60, 100 mesh) | 120.00 | 2.8571 |
| Cab-O-Sil M-5 ($SiO_2$) | 20.00 | 0.4762 |
| Lactose (Fast Flo) | 311.20 | 7.4095 |
| Avicel PH102 | 870.00 | 20.7143 |
| Crospovidone | 160.00 | 3.8095 |
| Stearic Acid | 120.00 | 2.8571 |
| Magnesium Stearate | 10.00 | 0.2381 |

The granulation batch was initially combined with all ingredients other than magnesium stearate and stearic acid, and blended to uniformity. Magnesium stearate and stearic acid were then added to the batch with further blending. The resulting powder mixture was compressed and tableted using standard tablet tooling. The tablets were coated with a 2.5% film coating of a hydroxypropyl methyl cellulose based aqueous film coating (Opadry, available from Colorcon of West Point, Pa.).

The tablets were assayed for triprolidine content and pseudoephedrine content by standard USP assays. The results are shown in Table A.

Example 3

Example 2 was repeated with the following ingredients substituted for those of Example 2:

| Ingredient | Quantity (grams) | Percent of Total |
| --- | --- | --- |
| Granulation Batch from Example 1 | 2488.80 | 59.2571 |
| Poloxamer 407 | 100.00 | 2.381 |
| Polyethlylene Oxide (N-60, 100 mesh) | 120.00 | 2.8571 |
| Sodium Lauryl Sulfate (washed and dried) | 10.00 | 0.2381 |
| Cab-O-Sil M-5 ($SiO_2$) | 20.00 | 0.4762 |
| Lactose (Fast Flo) | 311.20 | 7.4095 |
| Avicel PH102 | 860.00 | 20.4762 |
| Crospovidone | 160.00 | 3.8095 |
| Stearic Acid | 120.00 | 2.8571 |
| Magnesium Stearate | 10.00 | 0.2381 |

The tablets were assayed for triprolidine content and pseudoephedrine content by standard USP assays. The results are shown in Table A.

Comparative Example 1

A granulation batch was prepared with the following ingredients:

| Ingredient | Quantity (grams) | Percent of Total |
| --- | --- | --- |
| Triprolidine HCl | 150.00 | 2.00 |
| Pseudoephedrine HCl | 3600.00 | 48.00 |
| Lactose (Fast Flo) | 540.00 | 7.20 |
| Lactose (Fast Flo) | 3030.00 | 40.40 |
| Povidone (K29–32) | 135.00 | 2.40 |

All dry materials were delumped prior to use. All the materials except the povidone were dry blended. The povidone was added as a 30% aqueous solution and the batch mixed to uniformity. The wet granulation was wet sized and then dried. The dried granulation was sized to match the particle size of the remaining dry tablet ingredients. A portion of the resulting granulation batch was assayed for triprolidine content and pseudoephedrine content by standard USP assays. The results are shown in Table A.

Comparative Example 2

A granulation batch was prepared with the following ingredients:

| Ingredient | Quantity (grams) | Percent of Total |
| --- | --- | --- |
| Triprolidine HCl | 125.00 | 12.50 |
| Confectionery Sugar | 875.00 | 87.50 |

All dry materials were delumped prior to use and blended to uniformity. Water was added as the granulating agent and the batch was mixed. The wet granulation was wet sized and then dried. The dried granulation was sized to match the particle size of the remaining dry tablet ingredients.

The resulting granulation batch was used to prepare tablets having the following core ingredients:

| Ingredient | Quantity (grams) | Percent of Total |
| --- | --- | --- |
| Granulation Batch | 20.00 | 0.8125 |
| Pseudoephedrine HCl | 60.00 | 2.4375 |
| Poloxamer 407 | 5.00 | 0.2031 |
| Polyethylene Oxide (N-60, 100 mesh) | 6.00 | 0.2438 |
| Sodium Lauryl Sulfate | 0.50 | 0.0203 |
| Cab-O-Sil M-5 (SiO$_2$) | 20.00 | 0.8125 |
| Microcrystalline Cellulose | 1580.00 | 64.1855 |
| Crospovidone | 160.00 | 6.5001 |
| Pregelatinized Starch | 480.00 | 19.5003 |
| Stearic Acid | 120.00 | 4.8751 |
| Magnesium Stearate | 10.00 | 0.4063 |

The granulation batch was initially combined with all ingredients other than magnesium stearate and stearic acid, and blended to uniformity. Magnesium stearate and stearic acid were then added to the batch with further blending. The resulting powder mixture was compressed and tableted using standard tablet tooling. The tablets were coated with a 2.5% film coating of a hydroxypropyl methyl cellulose based aqueous film coating (Opadry).

The tablets were assayed for triprolidine content and pseudoephedrine content by standard USP assays. The results are shown in Table A.

Comparative Example 3

Comparative Example 2 was repeated with the following granulation batch substituted for that of Example 2:

| Ingredient | Quantity (grams) | Percent of Total |
| --- | --- | --- |
| Triprolidine HCl | 140.00 | 12.50 |
| Emdex | 980.00 | 87.50 |

The resulting tablets were assayed for triprolidine content and pseudoephedrine content by standard USP assays. The results are shown in Table A.

TABLE A

Assays of Active Ingredients

| SAMPLE | HPLC* ASSAY (%) | | DISSOLUTION ASSAY (%) | | | |
| --- | --- | --- | --- | --- | --- | --- |
| | TRP** | PSE*** | TRP 30 min | TRP 45 min | PSE 30 min | PSE 45 min |
| Example 1 | 97.2 | 96.8 | 98.8 | 98.8 | 101.4 | 101.9 |
| Comparative Example 1 | 106.4 | 100.7 | 87.7 | 86.8 | 98.7 | 98.9 |
| Example 2 | 97.6 | 98.8 | | 94.4 | | 99.6 |
| Example 3 | 96.5 | 92.8 | | 96.4 | | 98.9 |
| Comparative Example 2 | 104.0 | 100.2 | | 83.6 | | 90.9 |
| Comparative Example 3 | 105.2 | 100.7 | | 82.6 | | 98.9 |

*High Performance Liquid Chromatography
**Triprolidine
***Pseudoephedrine

Example 1 is a granulation including sodium chloride as the ionic additive, whereas Comparative Example 1 is a granulation devoid of an ionic additive according to the invention. Even though the granulation of Comparative Example 1 assays high for triprolidine using HPLC, the triprolidine content appears lower in the USP dissolution assay.

Examples 2 and 3 are tablets that include the granulation of Example 1, and differ from each other in that sodium lauryl sulfate, a wetting agent, is not included in the tablets of Example 2. Both show good dissolution in the USP assay.

Comparative Examples 2 and 3 are tablets devoid of an ionic additive according to the invention. These tablets show poor triprolidine availability in the USP assay despite the high percentage of triprolidine assayed by HPLC.

While the invention has been described in detail and with reference to specific examples thereof, it will be apparent to one skilled in the art that various changes and modifications can be made therein without departing from the spirit and scope thereof.

What is claimed is:

1. A process for preparing a pharmaceutical composition containing triprolidine, said process comprising:
   mixing said triprolidine and an ionic additive to provide said pharmaceutical composition, wherein said ionic additive is provided in an amount effective to increase triprolidine availability indicated by a dissolution assay.

2. The process of claim 1, wherein said composition further comprises a hydrogen bonding compound.

3. The process of claim 1, wherein said triprolidine is a salt of an acid.

4. The process of claim 3, wherein said triprolidine is triprolidine hydrochloride.

5. The process of claim 1, wherein said ionic additive is present in an amount effective to raise said triprolidine availability at least 5%.

6. The process of claim 1, wherein said ionic additive is present in an amount effective to raise said triprolidine availability at least 10%.

7. The process of claim 1, wherein said ionic additive is present in said composition in an amount effective to make at least 90% of said triprolidine available in solution.

8. The process of claim 1, wherein said ionic additive is present in said composition in an amount effective to make at least 94% of said triprolidine available in solution.

9. The process of claim 1, wherein said ionic additive is an alkali metal salt.

10. The process of claim 1, wherein said ionic additive is an alkali salt of a halogen.

11. The process of claim 1, wherein said ionic additive is a chloride salt of an alkali metal.

12. The process of claim 1, wherein said ionic additive is sodium chloride or potassium chloride.

13. The process of claim 1, wherein said ionic additive is present in an amount of about 10 to about 50 wt. %.

14. The process of claim 1, wherein said ionic additive is present in an amount of about 20 to about 40 wt. %.

15. The process of claim 1, wherein said ionic additive is present in an amount of about 26 to about 30 wt. %.

16. The process of claim 1, in a form of a tablet.

17. The process of claim 1, wherein said process further comprises:
    providing a wet granulation comprising said triprolidine and said ionic additive; and
    drying said wet granulation to provide said composition.

18. The process of claim 1, wherein said process further comprises directly compressing a mixture comprising said triprolidine and said ionic additive to provide said composition in a tablet form.

* * * * *